United States Patent [19]

Murdock et al.

[11]  4,314,061
[45]  Feb. 2, 1982

[54] CERTAIN 3,6-BIS-(HETEROAMINOALKOXY) ACRIDINES

[76] Inventors: Keith C. Murdock, 15 Birch St., Pearl River, N.Y. 10965; Martin R. Damiani, 603 Franklin Turnpike, Allendale, N.J. 07401; Frederick E. Durr, 387 Jefferson St., Ridgewood, N.J. 07450

[21] Appl. No.: 183,612

[22] Filed: Sep. 2, 1980

Related U.S. Application Data

[63] Continuation-in-part of Ser. No. 89,805, Oct. 31, 1979, abandoned, which is a continuation-in-part of Ser. No. 954,279, Oct. 24, 1978, abandoned, which is a continuation-in-part of Ser. No. 821,039, Aug. 1, 1977, abandoned.

[51] Int. Cl.$^3$ .................. C07D 413/14; C07D 219/08; C07D 241/04

[52] U.S. Cl. .................................. 544/80; 544/357; 546/104; 546/107; 424/250; 424/257; 424/248.4

[58] Field of Search .............. 546/104, 107; 544/361, 544/126, 80, 357

[56]  References Cited

U.S. PATENT DOCUMENTS 1,727,480  9/1929  Mietzsch ........................... 546/104
3,740,403  6/1973  Murdock ........................... 546/103

Primary Examiner—Alan L. Rotman

[57]  ABSTRACT

This disclosure describes compositions of matter useful for inducing the regression of tumors in warm-blooded animals and for enhancing the immune system, and the method of treatment of tumors and enhancing the immune response in mammals therewith, the active ingredients of said compositions of matter being certain 3,6-bis(aminoalkoxy)acridines or the pharmacologically acceptable acid-addition salts thereof.

13 Claims, No Drawings

CERTAIN 3,6-BIS-(HETEROAMINOALKOXY) ACRIDINES

CROSS REFERENCE TO RELATED APPLICATION

This application is a continuation-in-part of our co-pending application Ser. No. 89,805, filed Oct. 31, 1979, now abandoned, which is a continuation-in-part of our abandoned application Ser. No. 954,279, filed Oct. 24, 1978 which is a continuation-in-part of our abandoned application Ser. No. 821,039, filed Aug. 1, 1977.

BRIEF SUMMARY OF THE INVENTION

This invention is concerned with new compounds of the formula:

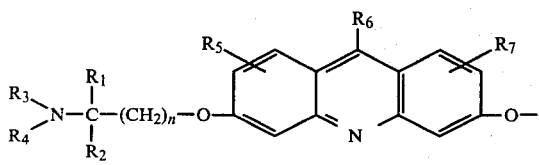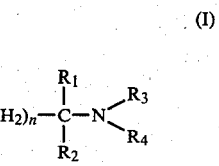

(I)

wherein n is the integer 1, 2 or 3; $R_1$ and $R_2$ are each hydrogen or methyl; $R_3$ and $R_4$ are the same or different and each may be hydrogen or straight chain or branched alkyl ($C_1$–$C_4$), or $R_3$ and $R_4$ taken together with the associated N(itrogen) may be pyrrolidino, piperidino, morpholino or N-methylpiperazino; $R_5$, $R_6$ and $R_7$ may be the same or different and are selected from the group consisting of hydrogen, fluoro, chloro, bromo and nitro with the proviso that when n is one or two and $R_1$ and $R_2$ are hydrogen or methyl and $R_3$ and $R_4$ are both lower alkyl then at least one of $R_5$, $R_6$ and $R_7$ must be a substituent other than hydrogen.

These novel substituted acridines form acid-addition salts with a variety of pharmaceutically acceptable organic and inorganic salt-forming reagents. These acid-addition salts, formed by admixture of the free base form of one of the acridines of the invention with one, two or three equivalents of an acid, suitably in a neutral solvent, are formed with such acids as sulfuric, phosphoric, hydrochloric, hydrobromic, nitric, citric, lactic, tartaric, acetic and related acids. For purposes of the present invention, the substituted 3,6-bis(aminoalkoxy)acridine free bases are equivalent to their non-toxic acid-addition salts.

These substituted 3,6-bis(aminoalkoxy)acridines may be readily prepared by treating one mole of the substituted 3,6-acridinediol disodium salt with two moles of an alkyl halide of the formula:

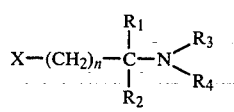

wherein x is chloro or bromo and $R_1$, $R_2$, $R_3$ and $R_4$ are as hereinabove defined. This reaction is preferably carried out in an inert solvent such as dimethylformamide at 75°–100° C., for a period of one hour or more. The product may be isolated by removing the inert solvent from the reaction mixture by evaporation, taking up the residue in water and extracting the aqueous phase with diethyl ether. Evaporation of the ether provides the product which may then be purified by chromatography.

Alternatively, the compounds may be prepared by reacting 3,6-acridinediol with 1,2- or 1,3-dihaloalkanes or 1-halo-2, or 3-hydroxysulfonyloxy alkanes in a solvent such as dimethylformamide for 15 minutes to 2 hours. The resulting bis(haloalkoxy)acridine can then be reacted with various amines or ammonia, preferably in a sealed bomb at 80°–150° C., for 10–50 hours. The product so isolated is purified as described above.

The 3,6-acridinediol disodium salts may be prepared as described in the literature by treating substituted 3,6-acridinediol with sodium hydride at room temperature in an inert solvent such as dimethylformamide for 15–30 minutes.

These acridine compounds also form complexes with metal atoms such as ferric chloride, zinc chloride, cuprous chloride, potassium hexachloroplatinate, chromic chloride and the like which are considered a part of this invention.

This invention is also concerned with the use of the compounds of formula (II) as antitumor agents and enhancers of the immune response:

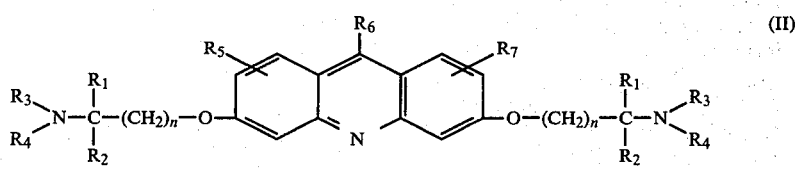

(II)

In the compounds of formula (II), n is an integer 1, 2 or 3; $R_1$ and $R_2$ are each hydrogen or methyl; $R_3$ and $R_4$ are the same or different and each may be hydrogen or straight chain or branched alkyl ($C_1$–$C_4$) or $R_3$ and $R_4$ taken together with the associated N(itrogen) may be pyrrolidino, piperidino, morpholino or N-methylpiperazino; $R_5$, $R_6$ and $R_7$ may be the same or different and are selected from the group consisting of hydrogen, fluoro, chloro, bromo and nitro; as well as the pharmaceutically acceptable salts thereof.

DETAILED DESCRIPTION OF THE INVENTION

In recent years, the concept of surgical-adjuvant chemotherapy for the treatment of solid neoplasms has become widely accepted by clinical oncologists. Surgery is an effective treatment modality for the removal of the bulk of a large primary tumor, but often is not applicable to the removal of small, widely scattered metastatic foci of disease. It is recognized that the principal cause of death of cancer patients is the growth of metastatic tumor foci. Systemic chemotherapy, as an adjunct to surgery, is ideally suited to the elimination of tumor metastases, and has been responsible for much of the progress made in the treatment of human solid tumors.

There are a variety of experimental animal tumor models that are used to assess the therapeutic effects of drugs on primary and metastatic tumor growth. The Lewis lung carcinoma is a highly malignant anaplastic murine carcinoma which when implanted subcutaneously gives rise to a large primary tumor that metastasizes to the lungs in the early stages of tumor growth. Surgical removal of the primary tumor is not curative unless performed within six days of tumor implantation, thereby preventing metastatic spread of tumor to the lungs. The actual cause of death of the experimental animals, even in the continued presence of the primary tumor, is the growth of the metastatic lung tumors. In this model system, therapeutic drug activity would be indicated by the inhibition of growth of the primary tumor (thereby preventing metastasis formation), or in conjunction with non-curative surgical removal of the primary tumor, by inhibiting the growth of lung metastases. This would be indicated by an increase in median survival time and an increase in the number of long term survivors (i.e. "cures") among drug treated mice when compared to mice that had received non-curative surgery and placebo instead of drug. Alternatively, the Lewis lung carcinoma can be implanted intraveneously in mice to establish "artificial" metastases in the lungs. Therapeutic drug activity, in this instance, would be reflected by an inhibition of the growth of these lung tumor metastases.

The B16 melanoma implanted subcutaneously in mice gives rise to a large primary tumor which metastasizes to many distant sites. Surgery is curative when carried out early during the growth of the primary tumor, before metastatic spread of the tumor has occured. Systemic chemotherapy in conjunction with non-curative surgery has been demonstrated to prevent metastatic tumor spread or to inhibit the growth of metastases formed prior to surgical removal of the primary tumor. Effective chemotherapy, in the latter instance, is indicated by an increased median survival time or an increased number of long term survivors (i.e. "cures") among drug treated mice when compared to placebo treated mice.

The compounds of the present invention are active when tested according to the following procedures:

(A) Antitumor Activity of Acridines Against Intravenously Inoculated Lewis Lung Carcinoma in Mice Lewis lung carcinoma cells, $5 \times 10^5$ viable cells, were injected intravenously into $BDF_1$ mice. The drug was prepared in normal saline and administered once daily, by the oral route, at doses ranging from 38 mg./kg to 400 mg/kg on days 1, 7, and 13 following tumor cell inoculation. A control group of mice received a saline placebo, instead of drug, by the oral route on the same days of treatment. All mice were sacrificed on day 19 following tumor inoculation, their lungs removed and individually weighed. Additionally, a group of 10 normal, non-tumor bearing $BDF_1$ mice, of the same sex, age, and body weight as the tumor bearing mice, were sacrificed and their lungs removed and weighed to determine the average normal lung weight. The average normal lung weight was subtracted from the weight of lungs from the tumored mice to determine the weight of tumorous tissue present in the lungs of the tumor bearing mice. A postive drug effect is indicated by a $\geq 58\%$ reduction in the average lung tumor weight of the drug treated mice, relative to the average lung tumor weight of the saline placebo treated mice. The results of this test on a representative compound of this invention appear in Table I below.

Reference to this animal model test system is:

(1) "Growth Characteristics and Chemotherapeutic Response of Intravenously Implanted Lewis Lung Carcinoma". Ovejera et al., Cancer Chemotherapy Reports Part 2, vol. 5:111-125, 1975.

TABLE I

Antitumor Activity of Acridines Against Intravenously Implanted Lewis Lung Carcinoma in Mice[1]

| Drug Treatment | Dose (MG/KG) | Route | Average[2] Lung Tumor Weight (mg) Day +19 | Average % Tumor Inhibition Day +19 | No. Survivors/ No. Treated Day +19 |
|---|---|---|---|---|---|
| Saline | | Oral | 147 | Control | 19/20 |
| 3,6-bis(2-diethyl-aminoethoxy)-acridine tri-hydrochloride | 400 | Oral | 12 | 92* | 10/12 |
| | 300 | " | 40 | 73* | 12/12 |
| | 150 | " | 72 | 51 | 12/12 |
| | 75 | " | 139 | 5 | 12/12 |
| | 38 | " | 99 | 33 | 10/12 |

[1]$BDF_1$ male mice inoculated intravenously with $5 \times 10^5$ Lewis lung tumor cells on day zero: 3,6-bis(2-diethylaminoethoxy)acridine trihydrochloride administered on days 1,7, and 13 after tumor inoculation.
[2]Average lung tumor weight = average weight of lungs from tumor bearing mice, minus average weight of lungs from normal, non-tumor bearing mice.
*Denotes significant ($\geq 58\%$) inhibition of lung tumor weight.

(B) Surgical-Adjuvant Antitumor Activity of Acridines Against Lewis Lung Carcinoma Implanted Subcutaneously in Mice $BDF_1$ mice were inoculated subcutaneously in the right hind footpad with $5 \times 10^5$ viable Lewis Lung carcinoma cells, on day zero. 3,6-bis(2-diethylaminoethoxy)acridine trihydrochloride was prepared in normal saline and administered by the oral route once daily, on days 1, 7, and 13 following tumor inoculation, at doses ranging from 50 mg/kg to 400 mg/kg. A control group of mice received a saline placebo instead of drug, and another group of tumor bearing mice received the positive control drug cyclophosphamide, at 100 mg/kg, administered by intraperitoneal injection. On the 11th day after tumor implantation, the mice were anesthesized with Nembutal, and the tumor bearing feet surgically amputated above the ankle joint. The surgical incision was swabbed with alcohol and sealed with stainless steel wound clips. The tumor bearing feet were individually weighed and the average weight of a normal foot (determined by weighing amputated feet from non-tumor bearing mice of the same age, sex and body weight) was subtracted to obtain the weight of tumor tissue in the amputated foot. Mice were then observed for deaths until the 90th day after tumor implantation. A therapeutic drug effect is indicated by; (a) a significant ($\geq 58\%$) inhibition of growth in the primary footpad tumor, (b) a significant ($\geq 25\%$) increase in life-span of drug treated mice, or (c) a statistically significant ($p < 0.05$) increase in the number of survivors at 90 days; i.e. "cures", relative to the placebo treated control group of mice. The results of this test appear in Table II below.

References to this animal model test system are:

(1) "Success and Failure in the Treatment of Solid Tumors. Cure of Metastatic Lewis Lung Carcinoma with Methyl-CCNU (NSC-95441) and Surgery-Chemotherapy". Mayo et al., Cancer Chemotherapy Reports 56:183–195, 1972.

(2) "Effectiveness of Clinically Active Antineoplastic Drugs in a Surgical-Adjuvant Chemotherapy Treatment Regimen Using the Lewis Lung (LL)Carcinoma". Merker et al., International Journal of Cancer 21:482–489, 1978.

intraperitoneal injection. On the 21st day after tumor implantation, the mice were anesthesized with Nembutal, and the tumor bearing feet were surgically amputated above the ankle joint. The surgical incision was swabbed with alcohol and sealed with stainless steel wound clips. The tumor bearing feet were individually weighed and the average weight of a normal foot (determined by weighing amputated feet from non-tumor bearing mice of the same sex, age, and body weight) was subtracted to obtain the weight of tumor tissue in the amputated feet. Mice were then observed for deaths

TABLE II

Surgical-Adjuvant Antitumor Activity of Acridines Against Lewis Lung Carcinoma Implanted Subcutaneously in Footpads of BDF$_1$ Mice[1]

| Drug | Dose (mg/kg) | Average[2] Tumor Weight In mg (Day + 11) | Average % of Tumor Weight Inhibition (Day + 11) | Median Survival Time (Days) | % Increased Life-Span | No. Survivors No. Treated (at + 90 days) |
|---|---|---|---|---|---|---|
| Saline | — | 379 | Control | 30.0 | — | 5/24 |
| 3,6-bis(2-diethyl-aminoethoxy)-acridine trihydrochloride | 400 | 17 | 96* | >90.0 | >200 + | 10/12** |
| | 300 | 56 | 85* | >90.0 | >200 + | 10/12** |
| | 200 | 38 | 90* | >90.0 | >200 + | 12/12** |
| | 100 | 203 | 46 | >90.0 | >200 + | 9/12** |
| | 50 | 236 | 38 | >90.0 | >200 + | 8/12 |
| Cyclophosphamide | 100 | 93 | 75* | >90.0 | >200 + | 10/12** |

[1]BDF$_1$ male mice inoculated subcutaneously in footpad with 5 × 10$^5$ Lewis lung tumor cells on day zero; 3,6-bis(2-diethylaminoethoxy)acridine trihydrochloride administered orally, and Cyclophosphamide intraperitoneally, on days 1, 7, and 13 following tumor implantation.
[2]Average tumor weight determined after surgical amputation of tumor bearing foot on day 11 following tumor implantation.
*Denotes significant ($\geq$58%) inhibition of primary tumor growth.
**Denotes significant (p < .05) increase in number of surviving mice, relative to saline control group.
+ Denotes significant ($\geq$25%) increase in life span of drug-treated mice, relative to saline control group.

(C) Surgical-Adjuvant Antitumor Activity of Acridines Against B16 Melanoma Implanted Subcutaneously in Mice BDF$_1$ mice were inoculated subcutaneously in the right hind footpad with 5×10$^5$ viable B16 melanoma cells, on day zero. The drug was prepared in normal saline and administered by the oral route once daily, on days 1, 7, and 13 following tumor implantation, at doses range from 50 mg/kg to 400 mg/kg. A control group of mice received a saline placebo instead of drug, and another group of tumor bearing mice received the positive control drug cyclophosphamide, at 100 mg/kg, by until the 90th day after tumor implantation. A therapeutic drug effect is indicated by: (a) a significant ($\geq$58%) inhibition of growth in the primary footpad tumor, (b) a significant ($\geq$25%) increase in the life-span of drug treated mice, or (c) a significant (p<0.05) increase in the number of survivors at +90 days, i.e. "cures", relative to the placebo treated control group of mice. The results of this test appear in Table III below.

Reference to this animal model test system is:

(1) "The Potential for Murine Tumor Models in Surgical Adjuvant Chemotherapy". Griswold, D. P. Jr., Cancer Chemotherapy Reports Part 2 vol. 5:187–204, 1975.

TABLE III

Surgical-Adjuvant Antitumor Activity of Acridines Against B16 Melanoma Implanted Subcutaneously in Footpads of BDF$_1$ Mice[1]

| Drug | Dose (mg/kg) | Average[2] Tumor Weight In mg (Day + 21) | Average % of Tumor Weight Inhibition (Day + 21) | Median Survival Time (Days) | % Increased Life-Span | No. Survivors No. Treated (at +90 days) |
|---|---|---|---|---|---|---|
| Saline | — | 603 | Control | 53.0 | — | 0/24 |
| 3,6 bis(2-diethyl-aminoethoxy)-acridine trihydrochloride | 400 | 51 | 92* | 69.0 | 30 + | 5/12** |
| | 300 | 63 | 90* | >90.0 | >70 + | 8/12** |
| | 200 | 122 | 80* | >90.0 | >70 + | 7/12** |
| | 100 | 225 | 63* | 64.0 | 21 | 2/12 |
| | 50 | 403 | 33 | 54.0 | 2 | 0/12 |
| Cyclophosphamide | 100 | 202 | 67* | >90.0 | >70 + | 7/12** |

[1]BDF$_1$ male mice inoculated with 5 × 10$^5$ B16 melanoma cells subcutaneously in footpad on day zero; 3,6-bis(2-diethylaminoethoxy)acridine trihydrochloride administered orally, and Cyclophosphamide intraperitoneally, on days 1, 7, and 13 following tumor implantation.
[2]Average tumor weight determined after surgical amputation of tumor bearing foot on day 21 following tumor implantation.
*Denotes significant ($\geq$58%) inhibit on primary tumor growth.
**Denotes significant (<0.05) increase in number of surviving mice, relative to saline control group.
+ Denotes significant ($\geq$25%) increase in life span of drug-treated mice, relative to saline control group.

TABLE IV

Effect of Acridines on Distribution of Metastatic Foci in Lungs of Mice Incolulated Subcutaneously with B16 Melanoma

| Drug | Dose (mg/kg) | No. of mice with lung metastases No. of lung foci/mouse | | | | |
|---|---|---|---|---|---|---|
| | | 0 | 1-5 | 6-10 | 11-15 | >15 |
| 0 | | 0 | 4 | 3 | 1 | 2 |
| Saline | | 0 | 3 | 3 | 1 | 0 |
| 3,6-bis(2-dimethyl-aminoethoxy)acridine trihydrochloride | 200 | All mice dead | | | | |
| | 100 | 3 | 7 | 0 | 0 | 0 |
| | 50 | 1 | 1 | 4 | 0 | 0 |
| | 25 | 2 | 4 | 2 | 1 | 0 |
| | 12.5 | 1 | 5 | 1 | 1 | 1 |
| | 6.5 | 0 | 3 | 3 | 1 | 1 |
| 5-fluorouracil | 50 | 2 | 4 | 3 | 0 | 0 |
| | 40 | 2 | 5 | 4 | 0 | 0 |
| | 30 | 3 | 3 | 3 | 0 | 0 |
| | 25 | 3 | 3 | 1 | 1 | 1 |
| | 20 | 1 | 2 | 1 | 2 | 1 |

$BDF_1$ male mice inoculated subcutaneously with 0.25 ml of a 10% tumor homogenate on day 0. Drugs administered intraperitoneally days 1,5,9 and 13; mice sacrificed on day 25, 10 mice per group. Distribution of metastatic foci from test results shown in Table 3.

(D) Potentiation of Cyclophosphamide Activity Against B-16 Melanoma in Mice $BDF_1$ male mice were inoculated subcutaneously with 0.25 ml. of a 10% B-16 melanoma homogenate. Cyclophosphamide was administered intraperitoneally at 80 mg./kg. the second day following the day of tumor implantation. Test compounds were given intraperitoneally on days +6, +8 and +10 relative to tumor implantation. Tumors were measured on day +26 with a positive response being indicated by a ≧50% inhibition of tumor size compared to the Cytoxan control. The compound 3,6-bis(2-diethylaminoethoxy)acridine trihydrochloride in combination with Cytoxan produced a 50% inhibition in local tumor growth, whereas monotherapy with either drug alone failed to do so. The results of this test appear in Table V.

TABLE V

Effect of Acridines in Combination with Cytoxan against B16 Melanoma in Mice

| Cyclo-phosph-amide (mg/kg) | 3,6-bis(2-diethyl-amino-ethoxy) acridine trihydro-chloride (mg/kg) | Average tumor weight (mg) Days after tumor inoculation | | $MST^5$ (days) | $ILS^5$ (%) |
|---|---|---|---|---|---|
| | | 21 | 26 | | |
| 0 | 0 | 3577 (7/10)[1] | 9989 (3/8) | 22.5 | |
| 80 | 0 | $1237^2$ (8/8) | 7458 (3/8) | 25.0 | 11 |
| 0 | 100 | $1892^2$ (7/8) | $4127^2$ (7/8) | 27.5 | 22 |
| 0 | 50 | $2168^2$ (7/8) | $3111^2$ (4/8) | 26.5 | 18 |
| | 25 | 2625 (7/8) | $6303^2$ (5/8) | 28.5 | 27 |
| 80 | 100 | 1532 (8/8) | $2836^3$ (5/8) | 27.5 | 22 |
| | 50 | 2041 (8/8) | $4258^3$ (7/8) | 28.5 | 27 |
| | 25 | 2029 (8/8) | $3125^{3,4}$ (6/8) | 29.5 | 31 |

$BDF_1$ male mice inoculated subcutaneously with 0.25 ml. of a 10% tumor homogenate on day 0. Drugs were administered intraperitoneally; cyclophosphoamide on day 2, 3,6-bis(2-diethylaminoethoxy)acridine trihydrochloride on days 6, 8 and 10.
[1]Number of survivors over number of mice treated.
[2]Significant at the p <0.05 level when compared to untreated controls.
[3]Significant at the p <0.05 level when compared to treatment with cyclophosphamide alone.
[4]Significant at the p <0.05 level when compared to treatment with either drug alone.
[5]MST = Median Survival Time
ILS = Percent increase in life span over control The use of immunomodulants and chemotherapeutic adjuvants constitutes a new therapeutic approach to the treatment of immune deficiencies and cancer and is based on the concept that there are distinctive antigens in or on most tumor cells (embryonal or transplantation antigens), that distinguish them from normal host cells. A majority of tumor immunologists favor the view that potentially malignant cells constantly arise but because of their "foreignness" they are normally eliminated by a competent humoral and cellular immune system. Occasionally however, tumor cells escape this immune surveillance and continue to reproduce and cancer results. The reason for the failure of the normally efficient immune surveillance mechanisms are not fully understood but it is thought that the immune system becomes less effective with increasing age. It is depressed in certain genetic immuno-deficiency diseases, in various bacterial, fungal or viral infections, and in patients undergoing immuno-suppressive therapy. The growth of the neoplasm itself, as well as the various therapeutic modalities designed to treat the disease, e.g., cytotoxic chemotherapy and radiation, leads to a still greater depression of host resistance and results in an increased susceptibility to both exogenous and endogenous infections and perhaps accounts for the re-initiation of tumor growth and metastasis which frequently follows treatment-induced tumor remission.

If depression of the immune system can result in the growth of malignancies, regulation of any facet of the immune response may help the host of eliminate residual cancer cells. Therefore, it is desirable to search for chemical agents (i.e., immunoregulants) capable of restoring and stimulating host immune defense mechanisms in order to overcome the deficiencies which account for susceptibility to disease and failure to eradicate the cancer. Such immunoregulating agents would likely be incapable of arresting the growth of a large tumor but their clinical utility would derive from their capacity to enhance normal immune surveillance mechanisms in patients whose tumor burden has been reduced by surgical, radiotherapeutic or chemotherapeutic methods.

Experimental studies in animals have demonstrated the antitumor potential of a number of immunoregulants including live organisms of bacillus Calmett-Guerin (BCG), heat-killed cells of Corynebacterium parvum, polynucleotides, and the anthelmintic drug, levamisole. These substances have been shown to stimulate cellular immunity and to produce tumor regression. Some successes have been claimed in early clinical trials with BCG against malignant melanoma and acute leukemia, and with levamisole against lung cancer and breast cancer. Although the antitumor effects produced by these agents have been promising, significant therapeutic benefits have yet to be realized. Since this is a new therapeutic approach, new drugs and methods of treatment must receive careful clinical evaluation in order to reveal their full potential.

Modern research is directed to the discovery of a drug similar to, but more potent than, known immunoregulants such as levamisole that would be effective in the eradication of tumor cells when used in conjunction with standard therapeutic measures. Stimulators of host resistance may be detected in animal models that can, in fact, detect both immunostimulators and anticancer agents. Mice are put in a condition simulating immunodepression common to cancer patients. This is accomplished by infecting mice with a leukemia virus which produces both leukemia and a disease-related immunodepression. Effective drugs are recognized by their ability to restore or enhance the antibody response in the experimental mice, or to inhibit tumor progression.

The active compounds and novel compositions of the present invention are active as immunomodulators when tested according to the following procedures:

(E) Inhibition of Splenomegaly and Restoration of Antibody Formation in Mice with Rauscher Virus-Induced Leukemia Infection of Balb/c mice with Rauscher leukemia virus (RLV) is characterized by: (1) a rapidly developing viremia, (2) suppression of the primary antibody response to antigens administered a few days after virus infection, (3) a progressive enlargment of the spleen (splenomegaly), and (4) death resulting from splenic rupture and hemorrhage. The protocol used to infect Balb/c mice with RLV and to test drugs for anticancer and/or immunostimulating activity is as follows:

Day 0: Inject 0.2 ml IP of a 20% (w/v) RLV-infected spleen cell extract into groups of 5 Balb/c mice. The spleen cell extract is prepared from mice infected with RLV 21 days previously.

Day +6, +7, +8: Test compounds are administered orally or by IP injection, in 0.5 ml of normal saline containing 0.2% Noble agar.

Day +7: Inject 0.5 ml IP of a thrice saline washed 10% suspension of sheep red blood cells (S-RBC).

Day +14: Bleed mice from the retro-orbital sinus; pool blood from each group. Sacrifice mice, remove and weigh spleens. Serum, harvested from pooled blood of each group of mice is stored at 4° C. for 24 hours. Hemagglutinin tests are performed by standard procedures using a microtiter technique. Acceptable hemagglutinin titer for leukemic (immunosuppressed) mice is ≦1:128. The positive control compound is Poly I:C (polyinosinic acid:polycytidylic acid) administered intraperitoneally on days +6, +7, and +8. Acceptable positive control hemagglutinin titers are 4-fold higher than the titers obtained in leukemic control mice. Average spleen weights of drug treated groups of mice are compared to the average spleen weight of the RLV-infected, placebo treated mice. Reference anticancer agents, cyclophosphamide, 5-fluorouracil, methotrexate, and 6-mercaptopurine consistently produce a 50% or greater reduction in splenomegaly.

Typical compounds of this invention are active in this test, in that they produce a 50% or greater reduction in splenomegaly, and a 4-fold or higher increase in hemagglutinin titer to sheep-RBC's, relative to the placebo treated, RLV-infected control mice. Results of this test appear in Tables VI and VII.

TABLE VI

Rauscher Virus-Induced Leukemia
% Reduction in Splenomegaly

| DRUG | % Reduction (mg/kg) |
| --- | --- |
| 3,6-Bis(2-diethylaminoethoxy)acridine trihydrochloride | 71(100)  68(50) |
| 3,6-Bis(2-ethylaminoethoxy)acridine trihydrochloride | 89(100) |
| 4,5-dichloro-3,6-bis(2-diethylaminoethoxy)acridine | 86(50) |
| 3,6-bis(2-diethylaminoethoxy)dinitroacridine | 108(100) |
| 3,6-bis(2-isopropylaminoethoxy)acridine trihydrochloride | 96(200) |
| 3,6-bis(3-piperidinopropoxy)acridine trihydrochloride | 74(50) |
| 3,6-bis(2-piperidinoethoxy)acridine trihydrochloride | 84(100) |
| Cyclophosphamide | 106(100) |

TABLE VI-continued

Rauscher Virus-Induced Leukemia
% Reduction in Splenomegaly

| DRUG | % Reduction (mg/kg) |
| --- | --- |
| 5-Fluorouracil | 115(50) |
| Methotrexate | 59(4) |
| 6-Mercaptopurine | 113(100) |

TABLE VII

Antibody Restoration in Mice With Rauscher Virus-Induced Leukemia

| DRUG | DOSE mg/kg | ROUTE | SERUM HEMAGGLUTININ TITER/SALINE CONTROL TITER |
| --- | --- | --- | --- |
| Poly I:C | 10 | IP | 1024/32 |
| Uninfected Controls | — |  | 2048 |
| 3,6-Bis(2-diethylaminoethoxy)acridine . 3HCl | 100 | IP | 512/32 |
| 4,5-dichloro-3,6-bis(2-diethylaminoethoxy)acridine | 100 | ORAL | 128/16 |
| 3,6-bis(2-isopropylaminoethoxy)acridine . 3HCl | 100 | ORAL | 512/32 |
| 3,6-bis(3-piperidinopropoxy)acridine . 3HCl | 50 | ORAL | 1024/32 |
| 3,6-bis(2-piperidinoethoxy)acridine . 3HCl | 100 | ORAL | 256/16 |

(F) Induction of Circulating Interferon in Mice

A single oral dose of 3,6-bis(2-diethylaminoethoxy)acridine trihydrochloride at 300 mg/kg induced the production of high levels of circulating interferon in normal $BDF_1$ mice. Peak titers of interferon were observed 16 to 24 hours after drug administration as shown in Table VIII. These peak titers declined rapidly, and were at normal levels 72 hours after drug treatment. The high levels of serum interferon induced in mice would be expected to provide protection against infection by viruses whose multiplication is prevented by interferon.

TABLE VIII

Induction of Circulating Interferon in $BDF_1$ Mice Following Oral Administration of Acridine

| Hours after 3,6-Bis(2-diethylaminoethoxy)-acridine trihydrochloride | Serum interferon titer[2] (units/ml) |
| --- | --- |
| 0 | 10 |
| 8 | 100 |
| 16 | 3200 |
| 24 | 3200 |
| 32 | 2100 |
| 48 | 50 |
| 72 | 10 |

[1]$BDF_1$ male mice received a single oral dose of 3,6-Bis(2-diethylaminoethoxy)acridine trihydrochloride at 300 mg/kg at zero time.
[2]Reciprocal of serum dilution producing a 50% reduction in cytopathic effects of vesicular stomatitis virus in murine L-929 cells.

(G) Antiviral Effects of Drugs Against an Interferon-Sensitive Virus, Columbia SK Taconic Farms male, white mice, weighing 18–24 g were treated by gavage, 18 hours before infection with a test compound suspended or dissolved in 1.0 ml of 0.2% aqueous agar solution. The mice were then infected by subcutaneous injection with one $LD_{95}$ of Columbia SK virus in 0.2 ml of distilled water. Groups of infected, untreated mice were used as controls to show the lethality of the infection. The test duration was 14 days. The results of this test on representative compounds of this invention appear in Table IX.

TABLE IX

Antiviral Effect of Drugs Against an Interferon - Sensitive Virus, Columbia SK

| DRUG | DOSE mg/kg (route) | Survivors/Total 14 Days Post Injection |
|---|---|---|
| 3,6-Bis(2-diethyl-aminoethoxy)acridine . 3HCl | 400 (Oral) | 10/15 |
| 3,6-Bis(2-ethyl-aminoethoxy)acridine . 3HCl | 400 (Oral) | 10/15 |
| 4,5-dichloro-3,6-bis(2-diethyl-aminoethoxy)acridine | 400 (Oral) | 7/15 |
| 3,6-Bis(2-isopropylaminoethoxy)-acridine . 3HCl | 400 (Oral) | 15/15 |
| 3,6-Bis(3-piperidinopropoxy)acridine . 3HCl | 400 (Oral) | 12/15 |
| 3,6-Bis(2-piperidinoethoxy)acridine . 3HCl | 400 (Oral) | 12/15 |
| 3,6-Bis(2-diethyl-aminopropoxy)acridine . 3HCl | 400 (Oral) | 13/15 |

(H) Protection of Mice Against Lethal Virus Infection By Oral Pre-Treatment With 3,6-Bis(2-diethylaminoethoxy)acridine Trihydrochloride Groups of 20 random-bred Swiss male mice were administered a single oral dose of 3,6-bis(2-diethylaminoethoxy)acridine trihydrochloride at 400 mg/kg, tilorone hydrochloride at 200 mg/kg, or a saline placebo. At 24, 48, 72 and 96 hours after drug treatment, separate groups of mice were injected SC with an $LD_{95}$ dose of the interferon sensitive virus, Columbia SK. Mice were observed for a period of 14 days post-virus infection to determine if drug pre-treatment produced a significant increase in survival relative to the survival of placebo-treated control mice. Typically, protection from lethal infection with Columbia SK virus is associated with induction of interferon. The results appear in Table X.

TABLE X

Efficacy of 3,6-Bis(2-diethylaminoethoxy)acridine Trihydrochloride Pre-Treatment of Mice Against Lethal Virus Challenge with an Interferon-Sensitive Virus, Columbia SK

| Oral treatment Time relative to virus challenge (hr.) | Survivors/Total (14 Days) | | |
|---|---|---|---|
| | 3,6-Bis(2-diethylamino-ethoxy)acridine trihydrochloride (400 mg/kg) | Tilorone (200 mg/kg) | Placebo controls |
| −24 | 19/20* | 18/20* | 5/20 |
| −48 | 10/20* | 15/20* | 1/20 |
| −72 | 1/20 | 9/20* | 0/20 |
| −96 | 1/20 | 8/20 | 1/20 |

*Significantly different survival ratios compared to placebo controls (p <.01)

(I) Stimulation of NK-cell Activity in Normal Mice

The existence of natural killer lymphocytes (NK cells) has recently been described in mice, rats and humans. NK cells derived from normal animals and humans mediate the rapid destruction of a wide variety of syngeneic and allogeneic tumor cells and virus infected cells, when tested in vitro. No prior exposure of the animal to tumor cells or viruses is required for NK cell-mediated target cell destruction. The resistance to growth of transplanted tumors in mice has been correlated with high levels of NK cell activity. The rapid rise in the level of NK cell activity in animals following infection with a variety of viruses, bacteria, or transplanted tumor cells suggests a possible role of NK cells in immune surveillance. It has recently been reported that administration of interferon inducers or interferon causes a rapid and substantial rise in the level of NK cell activity in mice. The results appear in Table XI.

References to this stimulation of NK cell activity are:
(1) J. Y. Djeu, J. A. Heinbaugh, H. T. Holden and R. B. Herberman, J. Immunology, 122, 174 (1979).
(2) S. Einhorn, H. Glomgren and H. Grander, Int. J. Cancer, 22, 405–412 (1978).
(3) Authors unknown, Nature, 273, 759 (1978).
(4) Authors unknown, Nature, 277, 221, (1979).

Test Procedure

Groups of 5–10 mice are administered test compounds or a placebo by oral, intraperitoneal, intravenous or subcutaneous routes. Approximately 18 hours later the mice are sacrificed and the spleens from each group of mice removed and pooled by groups. The pooled spleens are placed in 4° C. serum-free Eagle's minimum essential medium (MEM) and disrupted by gentle Dounce homogenization. The resulting single cell suspension is filtered through a 60 mesh nylon screen to remove debris and the cells are collected by centrifugation. The cell pellet is resuspended in 10 ml of hypotonic phosphate buffered saline (0.01 M sodium chloride+0.001 M potassium phosphate buffer, pH 7.0) for 5–10 seconds to lyse erythrocytes. A 40 ml portion of MEM supplemented with 10% fetal calf serum (MEM+F) is added and the cell suspension is filtered to remove aggregated debris. Spleen cells are collected by centrifugation, resuspended in MEM+F and the cell density adjusted to $1-2\times 10^7$ spleen cells per ml. of medium.

Human or murine tumor cells are used as targets of NK cell mediated cytolysis. Target cells are incubated in 0.5 ml. of MEM+F containing 50–100μ Ci of $^{51}$chromium (as sodium $^{51}$chromate). After incubation at 37° C. for 1–3 hours, target cells are washed with three 40 ml. volumes of cold MEM+F, to remove extracellular $^{51}$chromium. $^{51}$chromium-labelled target cells are resuspended in MEM+F at a cell density of $0.5-1\times 10^5$ per ml. of medium.

Triplicate assays of each cell suspension, derived from pooled spleens of test compound or placebo treated mice, are prepared to assess NK-cell activity. Spleen cells ($5\times 10^6$) and $^{51}$chromium-labelled target cells ($1\times 10^5$) are placed in plastic $10\times 75$ mm. Falcon tubes containing 1.0 ml. of MEM+F. The tubes are incubated at 37° C. for 4 hours, then chilled to 4° C. and centrifuged. Aliquots of cell-free supernatant medium are removed from each assay tube and the quantity of $^{51}$chromium released from lysed target cells is determined. A statistically significant increase in the quantity of $^{51}$chromium released in assays of spleen cells derived from drug treated mice, as compared to assays of spleen cells from placebo treated mice, indicates drug stimulation of NK cell activity. The compound 3,6-bis(2-diethylaminoethoxy)acridine trihydrochloride is active in this test, (as indicated in Table XI).

TABLE XI

Stimulation of Natural Killer Lymphocyte (NK-cell) Activity in Mice

| Compound[1] | Dose (mg/kg) | % Cytotoxicity Test 1 | % Cytotoxicity Test 2 |
|---|---|---|---|
| Saline | | 13.9 | 29.9 |
| 3,6-Bis(2-diethylamino- | 300 | 25.8*[2] | 38.2* |
| ethoxy)acridine tri- | 150 | 37.7** | 40.9** |
| hydrochloride | 75 | 29.5** | 44.4** |
| Poly I:C | 10 | 24.7* | 36.1 |

[1]Test compound administered orally and Poly I:C administered intraperitoneally to random-bred CD-1 mice (Test 1) or BDF$_1$ hybrids (Test 2), 18 hours prior to sacrifice of mice.
[2]*,**Indicates significant stimulation of NK-cell activity at (p <.05)* and (p <.01)**. Each treatment group mean was compared to the control mean (saline) using Student's t-test, with pooled variance estimate (pooled over all treatment groups for each day of test).

(J) Lack of Effect on Normal Mouse Bone Marrow

The effect of drugs on normal mouse bone marrow is evaluated by determining total cell counts of femurs and by the ability of surviving cells to form colonies in semi-solid medium. The test compound is administered orally and the reference drug Cytoxan is administered intraperitoneally to $C_{57}BL_6$ male mice. One femur from each of three mice per dose level is assayed 24 hours after treatment. Counts of nucleated cells are performed on pooled marrow suspensions and the clonogenic assay is performed by plating 50,000 cells in one ml. of culture medium in each of four culture dishes. The medium to support bone marrow progenitor cell growth is McCoy's medium supplemented with 0.9% methocel, 1.8% human serum albumin, 10% bovine fetal serum and 10% "conditioned" L-cell medium. Cultures are incubated at 37° C. in a humidified atmosphere and colonies are counted at seven days. The compound 3,6-bis(2-diethylaminoethoxy)acridine trihydrochloride had minimal effects on the total nucleated cell count while Cytoxan depressed the cell count significantly.

The compounds of the present invention are effective as immunomodulators (that is, they modulate the immune response) when administered orally in amounts ranging from about 5 mg. to about 400 mg. per kilogram of body weight per day. A preferred dosage regimen for optimum results would be from about 5 mg. to about 50 mg. per kilogram of body weight per day, and such dosage units are employed that a total of from about 350 mg. to about 3.5 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A practical advantage of this invention is that the active compound may be administered in any convenient manner such as the oral or buccal routes or it may be incorporated directly in the diet. p The novel compounds of this invention do possess antitumor activity in their own right, and are chemotherapeutic adjuvants. In addition, they potentiate the effect of anti-tumor agents and act as adjuvants to surgical therapy.

The compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.5% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound. The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

3,6-bis(2-diethylaminoethoxy)-4,5,-dichloro-2-nitroacridine

A 119.5 mg. portion of 3,6-bis(2-diethylaminoethoxy)-4,5-dichloroacridine is dissolved in one ml. of concentrated sulfuric acid. The solution is cooled in an ice bath and 60 mg. of potassium nitrate are added. The mixture is stirred at 0° C. for one hour, then at room temperature for 20 hours, poured into 20 ml. of ice water and the pH adjusted to 11.5 with 5 N sodium hydroxide. The mixture is then extracted three times with dichloromethane. The extracts are combined, dried over anhydrous sodium sulfate, filtered and concentrated in vacuo to a black gum. This gum is slurried in 25 ml. of boiling hexane and filtered. The filtrate is concentrated to 10 ml. and cooled in an ice bath. The crystals are collected and dried in vacuo, giving 54 mg. of the desired product, m.p. 100°–102° C.

EXAMPLE 2

3,6-bis(2-diethylaminoethoxy)-4,5-dinitroacridine

A 5.37 g. portion of 3,6-bis(2-diethylaminoethoxy)acridine trihydrochloride monohydrate is dissolved in 20 ml. of concentrated sulfuric acid. The solution is cooled in an ice bath and 2.22 g. of potassium nitrate are added. The mixture is stirred at 0° C. for one hour, then at room temperature for 18 hours, poured into 300 ml. of ice water and the pH adjusted to 12 with 10 N sodium hydroxide. The mixture is extracted three times with dichloromethane. The extracts are combined, washed with water, dried over anhydrous sodium sulfate, filtered and concentrated in vacuo, giving 4.3 g. of crude product. This material is purified by dry column chromatography on alumina using ethyl acetate as the developer. The compound is then recrystallized from methanol, giving 2.5 g. of the desired product, m.p. 138°–140° C.

EXAMPLE 3

3,6-bis(2-diethylaminoethoxy)-4,5-dichloroacridine

A 2.148 g. portion of 3,6-bis(2-diethylaminoethoxy)acridine trihydrochloride monohydrate is dissolved in 8 ml. of concentrated sulfuric acid. This solution is cooled in an ice bath and 1.175 g. of N-chlorosuccinimide are added. The procedure of Example 3 is followed giving 1.5 g. of a reddish brown crude product. This product is dissolved in 100 ml. of dichloromethane and filtered through a 2 inch×2½ inch bed of alumina. The filter bed is washed with one liter of dichloromethane, then one liter of ethyl acetate. The filtrates are combined, concentrated in vacuo and the residue is crystallized from 10 ml. of hexane giving 1.067 g. of the desired product as yellow crystals, m.p. 83°–84° C.

EXAMPLE 4

3,6-bis(2-diethylaminoethoxy)-4,5-dibromoacridine

The procedure of Example 3 is repeated, using 1.566 g. of N-bromosuccinimide in place of the N-chlorosuccinimide. The crude product is filtered through a 2½ inch×1½ inch Magnesol plug using 2 liters of ethyl acetate. The filtrate is concentrated in vacuo and the residue crystallized from 10 ml. of heptane, giving 0.921 g. of the desired product as yellow crystals, m.p. 66°–68° C.

EXAMPLE 5

3,6-bis(2-diethylaminoethoxy)-4,5-dichloro-1 (or, 7-dinitroacridine 3,6-bis(2-diethylaminoethoxy)-4,5-dichloroacridine is treated as described in Example 1, except that the mixture is heated at 80° C. for 16 hours resulting in the desired product.

EXAMPLE 6

3,6-bis(2-diethylaminoethoxy)-4,5-dibromo-2-(or 1)nitroacridine 3,6-bis(2-diethylaminoethoxy)-4,5-dibromoacridine is treated as described in Example 2, giving the desired product.

EXAMPLE 7

3,6-bis(2-diethylaminoethoxy)-4,5-dibromo-1-(or 2), 7-dinitroacridine 3,6-bis(2-diethylaminoethoxy)-4,5-dibromoacridine is treated as described in Example 5, giving the desired product.

EXAMPLE 8

3,6-bis(2-diethylaminoethoxy)-4,5-diacetamidoacridine 3,6-bis(2-diethylaminoethoxy)-4,5-dinitroacridine is reduced with hydrogen and palladium catalyst in acetic anhydride as the solvent in the reduction, giving the desired product.

EXAMPLE 9

3,6-bis(2-diethylaminoethoxy)-2(or 1)-nitroacridine 3,6-bis(2-diethylaminoethyl)-4,5-dibromo-2(or 1)nitroacridine is reduced with tri-n-butyltin hydride to give the desired product.

EXAMPLE 10

3,6-bis(2-diethylaminoethoxy)-2(or 1)-aminoacridine 3,6-bis(2-diethylaminoethoxy)-2(or 1)nitroacridine is reduced as described in Example 8 except using ethanol as solvent, giving the desired product.

EXAMPLE 11

3,6-bis(2-diethylaminoethoxy)-4,5-dihydroxyacridine 3,6-bis(2-diethylaminoethoxy)-4,5-diaminoacridine is diazitized with concentrated nitric/sulfuric acid giving the bis-diazonium salt which is then hydrolized by stirring in 5% aqueous sulfuric acid for 3 hours, giving the desired product.

EXAMPLE 12

3,6-bis(2-diethylaminoethoxy)-4,5-difluoroacridine 3,6-bis(2-diethylaminoethoxy)-4,5-diaminoacridine is diazotized as described in Example 11. The bis-diazonium salt is then treated with potassium tetrafluoroborate. The tetrafluoroborate salt is thermally decomposed to give the desired product.

EXAMPLE 13

3,6-bis(2-dimethylaminoethoxy)-1(or 2),7-dichloroacridine 3,6-bis(2-dimethylaminoethoxy)-1(or 2),7-diaminoacridine is diazotized with concentrated nitric/sulfuric acid. The bis-diazonium salt is treated with cuprous chloride giving the desired product.

EXAMPLE 14

3,6-bis(2-chloroethoxy)acridine hydrochloride

To a mixture of 2.36 g. of a 61.14% dispersion of sodium hydride in oil and 5.20 g. of 3,6-acridinediol sulfate is added 50 ml. of N,N-dimethylformamide. After stirring at room temperature for 40 minutes, 6.35 g. (4.57 ml.) of chloroethyl methanesulfonate are added to the reaction mixture. The mixture is stirred at room temperature for 2 hours, then at 50° C. for 2.5 hours, poured into 250 ml. of ice-water and placed in a freezer overnight. The resulting yellow crystals are collected and dissolved in 100 ml. of chloroform. To this solution is added 6 ml. of 6 N hydrochloric acid in isopropanol. Dilution of the chloroform solution with ether gives 2.8 g. of the desired product as yellow crystals, m.p. 228°–220° C.

EXAMPLE 15

3,6-bis(2-methylaminoethoxy)acridine trihydrochloride

A suspension of 1.5 g. of 3,6-bis(2-chloroethoxy) acridine hydrochloride in 100 ml. of methylamine is heated in a steel bomb at 80° C. for 24 hours. The excess methylamine is removed under reduced pressure. The chloroform solution containing the orange residue is washed with two 30 ml. portions of saturated aqueous sodium bicarbonate, then dried over sodium sulfate and filtered. The chloroform is removed, the residue is dissolved in 50 ml. of ethanol and 10 ml. of 6 N hydrochloric acid is isopropanol are added. This solution is heated to boiling, water is added until a clear solution is obtained and the solution is cooled, giving 1.25 g. of the desired product as orange crystals, m.p. 267°–269° C.

EXAMPLE 16

3,6-bis(2-n-propylaminoethoxy)acridine trihydrochloride

The compound is prepared from 3,6-bis(2-chloroethoxy)acridine hydrochloride and n-propylamine as described in Example 15, giving 1.20 g. of the desired product as yellow crystals, m.p. 250°–252° C.

EXAMPLE 17

3,6-bis(2-ethylaminoethoxy)acridine bishydrochloride

The compound is prepared from 3,6-bis(2-chloroethoxy-acridine hydrochloride and ethylamine as described in Example 15, giving 1.4 g. of the desired product as orange crystals, m.p. 253°–255° C.

EXAMPLE 18

3,6-bis(2-n-butylaminoethoxy)acridine trihydrochloride

The compound is prepared from 3,6-bis(2-chloroethoxy)acridine hydrochloride and n-butylamine as described in Example 15, giving 1.45 g. of the desired product as yellow crystals, m.p. 254°–256° C.

EXAMPLE 19

3,6-bis[2-(2-hydroxyethylamino)ethoxy]acridine

The compound is prepared from 3,6-bis(2-chloroethoxy)acridine hydrochloride and ethanolamine as described in Example 15, giving 0.7 g. of the desired product as yellow crystals, m.p. 125°–127° C.

EXAMPLE 20

3,6-bis[2-(2-hydroxyethylamino)ethoxy]acridine trihydrochloride

The compound 3,6-bis[2-(2-hydroxyethylamino)ethoxy] acridine is converted to the trihydrochloride salt as described in Example 15, giving 0.2 g. of the desired product as orange cryatals, m.p. 256°–258° C.

EXAMPLE 21

3,6-bis(2-aminoethoxy)acridine trihydrochloride

The compound is prepared from 3,6-bis(2-chloroethoxy)acridine hydrochloride and ammonia as described in Example 15, giving 0.3 g. of the desired product as orange crystals, m.p. 274°–275° C.

EXAMPLE 22

3,6-bis(2-isopropylaminoethoxy)acridine trihydrochloride

The compound is prepared from 3,6-bis(2-chloroethoxy)acridine hydrochloride and isopropylamine as described in Example 15, giving 1.1 g. of the desired product as yellow crystals, m.p. 232°–234° C.

EXAMPLE 23

3,6-bis(2-acetamidoethoxy)acridine 3,6-bis(2-aminoethoxy)acridine is treated with acetic anhydride/acetic acid followed by in vacuo removal of the volatiles, giving, after crystallization, the desired product.

EXAMPLE 24

3,6-bis(2-acetamideoethoxy)-4,5-dichloroacridine 3,6-bis(2-acetamidoethoxy)acridine is chlorinated as described in Example 1, giving the desired product.

EXAMPLE 25

3,6-bis(3-chloropropoxy)acridine hydrochloride

To a mixture of 11.80 g. of sodium hydride (61.14% oil dispersion) and 26.0 g. of 3,6-acridinediol sulfate (2:1) is added 250 ml. of dry N,N-dimethylformamide. The mixture is stirred at room temperature for 1.5 hours, then 49.8 g. of 3-chloropropyl-p-toluene sulfonate are added. This mixture is stirred at room temperature for 3 hours and 20 minutes, then at 50° C. for 2 hours. The volatile materials are removed under reduced pressure at 35°–40° C. and the residue is quenched with 1200 ml. of ice-cold saturated aqueous sodium bicarbonate solution. The resulting tan crystals are collected and dissolved in 500 ml. of chloroform. A 30 ml. portion of 6 N hydrochloric acid in isopropanol is added and the mixture is diluted with ether. The solid is collected and recrystallized from ether, giving the desired product as tan crystals, m.p. 211°–213° C.

EXAMPLE 26

3,6-bis(2-isopropylaminopropoxy)acridine trihydrochloride

The compound is prepared from 3,6-bis(3-chloropropoxy)acridine hydrochloride and isopropylamine as described in Example 15.

EXAMPLE 27

3,6-bis(3-diethylaminopropoxy)acridine trihydrochloride

The compound is prepared from 3,6-bis(3-chloropropoxy)acridine hydrochloride and diethylamine as described in Example 15 except that the mixture is heated at 100° C. for 24 hours, giving 1.5 g. of the desired product as yellow crystals, m.p. 235°–236° C.

EXAMPLE 28

3,6-bis(3-n-propylaminopropoxy)acridine trihydrochloride

The compound is prepared from 3,6-bis(3-chloropropoxy)acridine hydrochloride and m-propylamine as described in Example 15, giving 1.54 g. of the desired product as yellow crystals, m.p. 260°–262° C.

EXAMPLE 29

3,6-bis(3-n-butylaminopropyl)acridine trihydrochloride

The compound is prepared from 3,6-bis(3-chloropropoxy)acridine hydrochloride and n-butylamine as described in Example 15, giving 2.0 g. of the desired product as orange crystals, m.p. 247°–249° C.

EXAMPLE 30

3,6-bis(3-ethylaminopropoxy)acridine trihydrochloride

The compound is prepared from 3,6-bis(3-chloropropoxy)acridine hydrochloride and ethylamine as described in Example 15, giving 1.4 g. of the desired product as yellow crystals, m.p. 265°–266° C.

EXAMPLE 31

3,6-bis(3-methylaminopropoxy)acridine trihydrochloride

The compound is prepared from 3,6-bis(3-chloropropoxy)acridine hydrochloride and methylamine as described in Example 15, giving 1.4 g. of the desired product as yellow crystals, m.p. 285°–287° C.

EXAMPLE 32

3,6-bis(4-aminobutoxy)acridine trihydrochloride

The compound is prepared from 3,6-bis(4-chlorobutoxy)acridine hydrochloride and ammonia as described in Example 15.

EXAMPLE 33

3,6-bis(2-diethylaminoethoxy)acridine-ferric chloride complex

A suspension of 3,6-bis(2-diethylaminoethoxy)acridine trihydrochloride and one equivalent of ferric chloride in ethanol is refluxed for 2 hours, concentrated and cooled giving the desired product as crystals which correspond to a 1:1 complex.

EXAMPLE 34

3,6-bis(2-diethylaminoethoxy)acridine zinc chloride complex

A suspension of 3,6-bis(2-diethylaminoethoxy)acridine free base and one equivalent of zinc chloride in ethanol is refluxed for 2 hours. The mixture is precipitated with ethyl acetate giving the 1:1 complex.

EXAMPLE 35

3,6-bis(2-diethylaminoethoxy)acridine-platinum chloride complex

A suspension of 3,6-bis(2-diethylaminoethoxy)acridine trihydrochloride and one equivalent of potassium hexachloroplatinate is refluxed in ethanol. The precipitate is collected giving the desired 1:1 complex.

EXAMPLE 36

3,6-bis(2-diethylaminoethoxy)acridine-chromium chloride complex

A suspension of 3,6-bis(2-diethylaminoethoxy)acridine and one equivalent of chromium chloride in ethanol is refluxed for 2 hours. The solvent is removed giving the desired 1:1 complex.

EXAMPLE 37

3,6-bis(2-diethylaminoethoxy)acridine-cupric chloride complex

A suspension of 3,6-bis(2-diethylaminoethoxy)acridine trihydrochloride and one equivalent of cupric chloride in ethanol is refluxed for 2 hours. Concentration and cooling gives the 1:1 adduct.

EXAMPLE 38

3,6-bis(2-dimethylaminoethoxy)acridine-cobalt complex

A suspension of 3,6-bis(2-dimethylaminoethoxy)acridine trihydrochloride and one equivalent of cobalt nitrate in ethanol is refluxed for 2 hours. The solid is collected giving the desired 1:1 complex.

EXAMPLE 39

3,6-bis(2-aminoethoxy)acridine-copper complex

A suspension of 3,6-bis(2-aminoethoxy)acridine and one equivalent of cupric chloride in ethanol is refluxed for 2 hours. Solvent removal gives the desired adduct.

EXAMPLE 40

3,6-bis(2-dimethylaminopropoxy)acridine-iron complex

A suspension of 3,6-bis(2-dimethylaminopropoxy)acridine and one equivalent of ferric chloride in ethanol is refluxed for 2 hours. Solvent removal gives the desired complex.

EXAMPLE 41

2,6-bis(2-diethylaminoethoxy)-2(or 1)-amino-4,5-dichloroacridine

The compound is prepared from 3,6-bis(2-diethylaminoethoxy)-2-nitro-4,5-dichloroacridine by reduction as described in Example 10.

EXAMPLE 42

3,6-bis[2-(4-methyl-1-piperazinyl)ethoxy]acridine

The compound is prepared from 3,6-bis(2-chloroethoxy)acridine hydrochloride and N-methylpiperazine as described in Example 15, except that the mixture is heated at 100° C. for 24 hours to attain reaction and that the free base is isolated.

EXAMPLE 43

3,6-bis[2-(1-morpholino)ethoxy]acridine

The compound is prepared from 3,6-bis(2-chloroethoxy)acridine hydrochloride and morpholine as described in Example 42.

EXAMPLE 44

3,6-bis[3-(1-piperidino)ethoxy]acridine

The compound is prepared from 3,6-bis(3-chloroethoxy)acridine hydrochloride and piperidine as described in Example 27, except that the free base is isolated.

EXAMPLE 45

3,6-bis[3-(1-piperidino)propoxy]acridine trihydrochloride

The trihydrochloride salt of 3,6-bis[3-(1-piperidino)propoxy]acridine is prepared as described in Example 15.

EXAMPLE 46

3,6-bis[3-(1-pyrrolyl)propoxy]acridine

The compound is prepared from 3,6-bis(3-chloropropoxy)acridine hydrochloride and pyrrole as described in Example 44.

EXAMPLE 47

3,6-bis[3-(4-methyl-1-piperazinyl)propoxy]acridine

The compound is prepared from 3,6-bis(3-chloropropoxy)acridine hydrochloride and N-methylpiperazine as described in Example 44.

EXAMPLE 48

3,6-bis(4-chlorobutoxy)acridine hydrochloride

To a mixture of 11.8 g. of sodium hydride (61.1% dispersion in oil) and 26.0 g. of 3,6-acridinediol is added 250 ml. of dimethylformamide. The mixture is stirred at room temperature for 1.5 hours, then 52.5 g. of 4-chlorobutyl-p-toluenesulfonate are added. This mixture is stirred at room temperature for 3 hours and 20 minutes and then at 50° C. for 2 hours. The volatile materials are removed under reduced pressure at 35°–40° C. The residue is quenched with 1200 ml. of ice-cold saturated aqueous sodium bicarbonate. The resulting tan crystals are collected and dissolved in 500 ml. of chloroform, 30 ml. of 6 N hydrochloric acid in isopropanol are added and the mixture is diluted with ether, giving the desired product as the hydrochloride salt.

EXAMPLE 49

3,6-bis(4-diethylaminobutoxy)acridine trihydrochloride

A mixture of 2.0 g. of 3,6-bis(4-chlorobutoxy) acridine hydrochloride and 150 ml. of diethylamine is heated in a steel bomb at 100° C. for 24 hours. The excess diethylamine is removed under reduced pressure. The residue is dissolved in 150 ml. of chloroform and this chloroform solution is washed with two 30 ml. portions of saturated aqueous sodium bicarbonate, then dried over sodium sulfate and filtered. The chlorofrom is evaporated and the residue is dissolved in 50 ml. of absolute ethanol. A 10 ml. portion of 6 N hydrochloric acid in isopropanol is added giving the desired product as yellow crystals.

EXAMPLE 50

3,6-bis(4-methylaminobutoxy)acridine trihydrochloride

The compound is prepared from 3,6-bis(4-chlorobutoxy)acridine hydrochloride and methylamine as described in Example 15.

EXAMPLE 51

3,6-bis(4-chloro-2-methylbutoxy)acridine hydrochloride

The compound is prepared from 3,6-acridinediol and 4-chloro-2-methyl-1-butanolmethane sulfonate as described in Example 25.

EXAMPLE 52

3,6-bis(4-dimethyl-2-methylbutoxy)acridine trihydrochloride

The compound is prepared from 3,6-bis(4-chloro-2-methylbutoxy)acridine hydrochloride and dimethylamine as described in Example 27.

EXAMPLE 53

3,6-bis(4-amino-2-methylbutoxy)acridine hydrochloride

The compound is prepared from 3,6-bis(4-chloro-2-methylbutoxy)acridine hydrochloride and ammonia as described in Example 15.

EXAMPLE 54

4,5-dichloro-3,6-bis[3-(1-piperidino)propoxy]acridine

The compound is prepared from 3,6-bis[3-(1-piperidino)propoxy]acridine and N-chlorosuccinimide as described in Example 3.

EXAMPLE 55

4,5-dibromo-3,6-bis[2-(1-piperidino)ethoxy]acridine

The compound is prepared from 3,6-bis[2-(1-piperidino)ethoxy]acridine and N-bromosuccinimide as described in Example 4.

EXAMPLE 56

4,5-dichloro-2,3-bis[2-(1-piperidino)ethoxy]acridine

The compound is prepared from 3,6-bis[2-(1-piperidino)ethoxy]acridine and N-chlorosuccinimide as described in Example 3.

EXAMPLE 57

3,6-bis[4-(1-piperidino)butoxy]acridine trihydrochloride

The compound is prepared from 3,6-bis(4-chlorobutoxy)acridine hydrochloride and piperidine as described in Example 44.

EXAMPLE 58

3,6-bis[4-(1-piperidino)-2-methylbutoxy]acridine trihydrochloride

The compound is prepared from 3,6-bis(4-chloro-2-methylbutoxy)acridine hydrochloride and piperidine as described in Example 44.

EXAMPLE 59

3,6-bis[2-(1-pyrrolyl)ethoxy]acridine trihydrochloride

The compound is prepared from 3,6-bis(2-chloroethoxy)acridine hydrochloride and pyrrole as described in Example 46.

EXAMPLE 60

4,5-dichloro-3,6-bis[2-(1-pyrrolyl)ethoxy]acridine

The compound is prepared from 3,6-bis[2-(1-pyrrolyl)ethoxy]acridine trihydrochloride and N-chlorosuccinimide as described in Example 3.

We claim:

1. A compound selected from the group consisting of those of the formula:

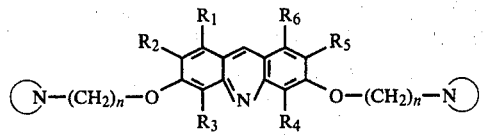

wherein n is the integer 2, 3 or 4; $R_1$, $R_2$, $R_3$, $R_4$, $R_5$ and $R_6$ are each individually selected from the group consisting of hydrogen, hydroxy, fluoro, chloro, bromo, nitro, amino and acetamido; and

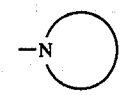

is 1-pyrrolidino, 1-piperidino, 1-morpholino or 4-methyl-1-piperazino; and the pharmacologically acceptable acid-addition salts thereof.

2. The compound according to claim 1 wherein n is 2; $R_1$, $R_2$, $R_3$, $R_4$, $R_5$ and $R_6$ are all hydrogen; and

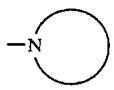

is 4-methyl-1-piperazino; 3,6-bis[2-(4-methyl-1-piperazino)ethoxy]acridine.

3. The compound according to claim 1 wherein n is 2; $R_1$, $R_2$, $R_3$, $R_4$, $R_5$ and $R_6$ are all hydrogen; and

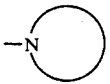

is 1-morpholino; 3,6-bis[2-(1-morpholino)ethoxy]acridine.

4. The compound according to claim 1 wherein n is 2; $R_1$, $R_2$, $R_3$, $R_4$, $R_5$ and $R_6$ are all hydrogen; and

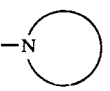

is 1-piperidino; 3,6-bis[2-(1-piperidino)ethoxy]acridine.

5. The compound according to claim 1 wherein n is 3; $R_1$, $R_2$, $R_3$, $R_4$, $R_5$ and $R_6$ are all hydrogen; and

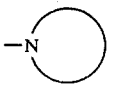

is 1-piperidino; 3,6-bis[3-(1-piperidino)propoxy]acridine trihydrochloride.

6. The compound according to claim 1 wherein n is 3; $R_1$, $R_2$, $R_3$, $R_4$, $R_5$ and $R_6$ are all hydrogen; and

is 1-pyrrolidino; 3,6-bis[3-(1-pyrrolidino)propoxy]acridine.

7. The compound according to claim 1 wherein n is 3; $R_1$, $R_2$, $R_3$, $R_4$, $R_5$ and $R_6$ are all hydrogen; and

is 4-methyl-1-piperzino; 3,6-bis[3-(4-methyl-1-piperazino)propoxy]acridine.

8. The compound according to claim 1 wherein n is 3; $R_3$ and $R_4$ are both chloro; $R_1$, $R_2$, $R_5$ and $R_6$ are all hydrogen; and

is 1-piperidino; 4,5-dichloro-3,6-bis[3-(1-piperidino)propoxy]acridine.

9. The compound according to claim 1 wherein n is 2; $R_3$ and $R_4$ are both bromo; $R_1$, $R_2$, $R_5$ and $R_6$ are all hydrogen; and

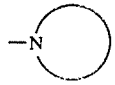

is 1-piperidino; 4,5-dibromo-3,6-bis[2-(1-piperidino)ethoxy]acridine.

10. The compound according to claim 1 wherein n is 2; $R_3$ and $R_4$ are both chloro; $R_1$, $R_2$, $R_5$ and $R_6$ are all hydrogen; and

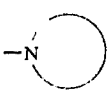

is 1-piperidino; 4,5-dichloro-3,6-bis[2-(1-piperidino)ethoxy]acridine.

11. The compound according to claim 1 wherein n is 4; $R_1$, $R_2$, $R_3$, $R_4$, $R_5$ and $R_6$ are all hydrogen; and

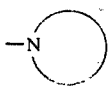

is 1-piperidino; 3,6-bis[4-(1-piperidino)butoxy]acridine trihydrochloride.

12. The compound according to claim 1 wherein n is 2; $R_1$, $R_2$, $R_3$, $R_4$, $R_5$ and $R_6$ are all hydrogen; and

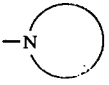

is 1-pyrrolidino; 3,6-bis[2-(1-pyrrolidino)ethoxy]acridine trihydrochloride.

13. The compound according to claim 1 wherein n is 2; $R_3$ and $R_4$ are both chloro; $R_1$, $R_2$, $R_5$ and $R_6$ are all hydrogen; and

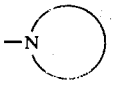

is 1-pyrrolidino; 4,5-dichloro-3,6-bis-[2-(1-pyrrolidino)ethoxy]acridine.

* * * * *